United States Patent [19]

Kuroda

[11] Patent Number: 5,656,112
[45] Date of Patent: Aug. 12, 1997

[54] SYNTHETIC RESIN CONTAINER INCLUDING A MOUTHPIECE SEALED BY A CLOSURE AND A METHOD FOR SEALING THE SAME

[75] Inventor: Nihee Kuroda, Osaka, Japan

[73] Assignee: Fuso Pharmaceutical Industries, Inc., Osaka, Japan

[21] Appl. No.: 266,484

[22] Filed: Jun. 27, 1994

[30] Foreign Application Priority Data

Jul. 9, 1993 [JP] Japan ................... 5-170053

[51] Int. Cl.6 ........................................... B65B 7/28
[52] U.S. Cl. ..................... 156/69; 53/486; 53/488; 156/322
[58] Field of Search ..................... 156/69, 308.2, 156/309.6, 321, 322; 53/478, 479, 486, 488, 489

[56] References Cited

U.S. PATENT DOCUMENTS

| | | | |
|---|---|---|---|
| 4,222,974 | 9/1980 | Smith | 156/308.2 |
| 4,259,419 | 3/1981 | Uba | 53/489 |
| 4,769,095 | 9/1988 | Sager | 53/488 |
| 4,984,415 | 1/1991 | Kuroda | 156/69 |
| 5,160,061 | 11/1992 | Stolzman | 156/69 |

FOREIGN PATENT DOCUMENTS 3-28944  4/1991  Japan.

*Primary Examiner*—Daniel Stemmer
*Attorney, Agent, or Firm*—Wenderoth, Lind & Ponack

[57] ABSTRACT

A synthetic resin container including a mouthpiece sealed by a closure is to be used for medical drip infusion or the like. The closure has a tight-sealing synthetic resin stopper, and a leakage preventing rubber stopper for preventing liquid leakage when the closure is pierced by a needle or the like. The mouthpiece of the synthetic resin container is sealed by the closure according to a method including providing a concave portion and/or a convex portion having a cross-section shaped in a wedge or the like at one or both of the upper portions of the mouthpiece and the tight-sealing synthetic resin stopper in order to impart provided thermal conductivity. The synthetic resin stopper is inserted into the mouthpiece and the rubber stopper is inserted into the synthetic resin stopper. The upper portions of the mouthpiece and the synthetic resin stopper are covered with a metallic mouthpiece forming cap. Then the metallic mouthpiece forming cap is pressed using only heat generated at the mouthpiece of the container during molding of the container so that the mouthpiece and the synthetic resin stopper are pressed inwardly and are thermally welded so as to be integrated with each other and with the rubber stopper.

2 Claims, 4 Drawing Sheets

SYNTHETIC RESIN CONTAINER INCLUDING A MOUTHPIECE SEALED BY A CLOSURE AND A METHOD FOR SEALING THE SAME

BACKGROUND OF THE INVENTION

1. Field of the Invention

The present invention relates to a synthetic resin container including a mouthpiece sealed by a closure, and a method for sealing the same. More specifically, it relates to a synthetic resin container including a mouthpiece sealed by a closure to be used for medical drip infusion or the like. The closure includes a tight-sealing synthetic resin stopper and a leakage preventing rubber stopper, and a method for sealing the same.

2. Description of the Prior Art

A synthetic resin container to be used for medical drip infusion or the like should be sealed by a closure capable of preventing liquid leakage even when an instillation needle or the like is inserted through the closure or is pulled out. To satisfy the above requirement, for example, a closure having a tight-sealing synthetic resin stopper and a leakage preventing rubber stopper has been employed.

Hitherto, such a synthetic resin container has been disclosed in, for example, Japanese Patent KOKOKU No. 3-28944, by the same inventor of the present invention. To seal the mouthpiece of the conventional synthetic resin container, first, the synthetic resin stopper is inserted into the mouthpiece, and the rubber stopper is then inserted into the synthetic resin stopper. Next, the top surfaces of the mouthpiece and the synthetic resin stopper, which are made flat, are covered with a metallic mouthpiece forming cap. Finally, by pressing the metallic mouthpiece forming cap using a welding heater, the mouthpiece and the synthetic resin stopper are pressed inwardly and thermally welded and integrated with each other and with the rubber stopper.

However, according to the prior art, each of the mouthpiece and the synthetic resin stopper has a flat top or upper surface. That is, the upper portions of the mouthpiece and the synthetic resin stopper are both solid. Due to such a configuration where two circular cylinders are solid, the thermal conductivity between the two circular cylinders is inferior. Thus, a problem arises because a long period of time is required for the thermal welding process.

Furthermore, the thermal welding process necessitates a welding heater and an additional power source. Thus, another problem arises in that the thermal welding process becomes complicated and consumes expressive energy.

SUMMARY OF THE INVENTION

The present invention addresses the problems associated with the conventional thermal welding process. As described above, conventional welding processes require long periods of time because the upper portions of the mouthpiece and the synthetic resin stopper are solid. The present invention overcomes the problems associated with conventional processes.

Therefore, an object of the present invention is to provide a method for sealing a mouthpiece of a synthetic resin container by a closure. The closure includes a tight-sealing synthetic resin stopper and a leakage preventing rubber stopper. The method comprises providing a concave portion and/or convex portion at one or both of upper portions of the mouthpiece and the tight-sealing synthetic resin stopper. The concave or convex portions have cross-sectional shapes in the form of a wedge or the like. The method also includes inserting a tight-sealing synthetic resin stopper in the mouthpiece and then inserting a leakage preventing rubber stopper in the tight-sealing synthetic resin stopper. A metallic mouthpiece forming cap is provided to cover the upper portions of the mouthpiece and the tight-sealing synthetic resin stopper. Then the mouthpiece and the tight-sealing synthetic resin stopper are pressed inwardly and thermally welded so as to be integrated with each other and with the leakage preventing rubber stopper by the metallic cap and a welding heater.

Another object of the present invention is to provide a synthetic resin container including a mouthpiece sealed by a closure according to the above method.

Still another object of the present invention is to provide a method for sealing a mouthpiece of a synthetic resin container with a closure. The closure includes a tight-sealing synthetic resin stopper and a leakage preventing rubber stopper. The method of sealing includes providing a concave portion and/or a convex portion at the upper portion of the tight-sealing synthetic resin stopper. The concave or convex portions have a cross-section in the shape of a wedge or the like. The tight-sealing synthetic resin stopper is inserted in the mouthpiece and the leakage preventing rubber stopper is inserted in the tight-sealing synthetic resin stopper. The upper portions of the mouthpiece and the tight-sealing synthetic resin stopper are covered with a metallic mouthpiece forming cap and the cap is pressed utilizing only heat generated at the mouthpiece when the mouthpiece is thermosoftened during a container molding process. The mouthpiece and the tight-sealing synthetic resin stopper are pressed inwardly and are thermally welded so as to be integrated with each other and with the leakage preventing rubber stopper.

Still further another object of the present invention is to provide a synthetic resin container including a mouthpiece sealed by a closure according to the above method.

To achieve the above objects, the present invention improves the synthetic resin container sealed by the closure of Japanese Patent KOKOKU No. 3-28944 by including a step of providing a concave portion and/or a convex portion having a cross-section shaped in the form of a wedge or the like at one or both of the upper portions of the mouthpiece and the tight-sealing synthetic resin stopper. Thereafter, the synthetic resin stopper and the rubber stopper are inserted in the mouthpiece of the synthetic resin container successively. Then the upper portions of the mouthpiece and the synthetic resin stopper are covered with a metallic mouthpiece forming cap. Finally the metallic mouthpiece forming cap is pressed using a heater so that the mouthpiece and the synthetic resin stopper are thermally welded so as to be integrated with each other and with the rubber stopper. Thus, the mouthpiece and closure can be thermally welded so as to be integrated with each other in a shorter period of time as compared with the prior art.

According to the present invention, at least one of the upper portions of the mouthpiece and the synthetic resin stopper is concave or convex, i.e., the material at the upper portions is reduced, thereby resulting in improved thermal conductivity between the upper portions of the mouthpiece and the synthetic resin stopper.

With the improved thermal conductivity, the mouthpiece and the synthetic resin stopper, both of which are made of synthetic resin, can readily be thermally welded so as to be integrated with each other and with the rubber stopper in a shorter period of time than in the prior art. Thus, it is possible to improve the production efficiency and to employ a mass-production system.

According to another aspect of the present invention, the mouthpiece and the closure can be integrated with each other without using the welding heater. In detail, a concave portion and/or a convex portion having a cross-section shaped in the form of a wedge or the like, is provided at the upper portion of the synthetic resin stopper of the closure, thereby imparting excellent thermal conductivity. In this case, the mouthpiece may also be provided with a concave portion and/or a convex portion having a cross-section shaped in the form of a wedge or the like. With the improved thermal conductivity, the mouthpiece and the synthetic resin stopper can be thermally welded when they are pressed inwardly with a metallic mouthpiece forming cap or the like, only using heat generated at the mouthpiece during a container molding process, i.e., during a time when the mouthpiece is thermosoftened during the container molding process. As a result, the mouthpiece and the synthetic resin stopper can be integrated with each other and with the rubber stopper, only using the heat generated at the mouthpiece of the synthetic resin container, thereby saving energy and simplifying the production process.

The above and further objects, features and advantages of the invention will more apparent from the following description with reference to the accompanying drawings. It is to be expressly understood, however, that the drawings are for purpose of illustration only and are not intended as a definition of the limits of the invention.

DETAILED DESCRIPTION OF THE PREFERRED EMBODIMENTS

Figure 1:
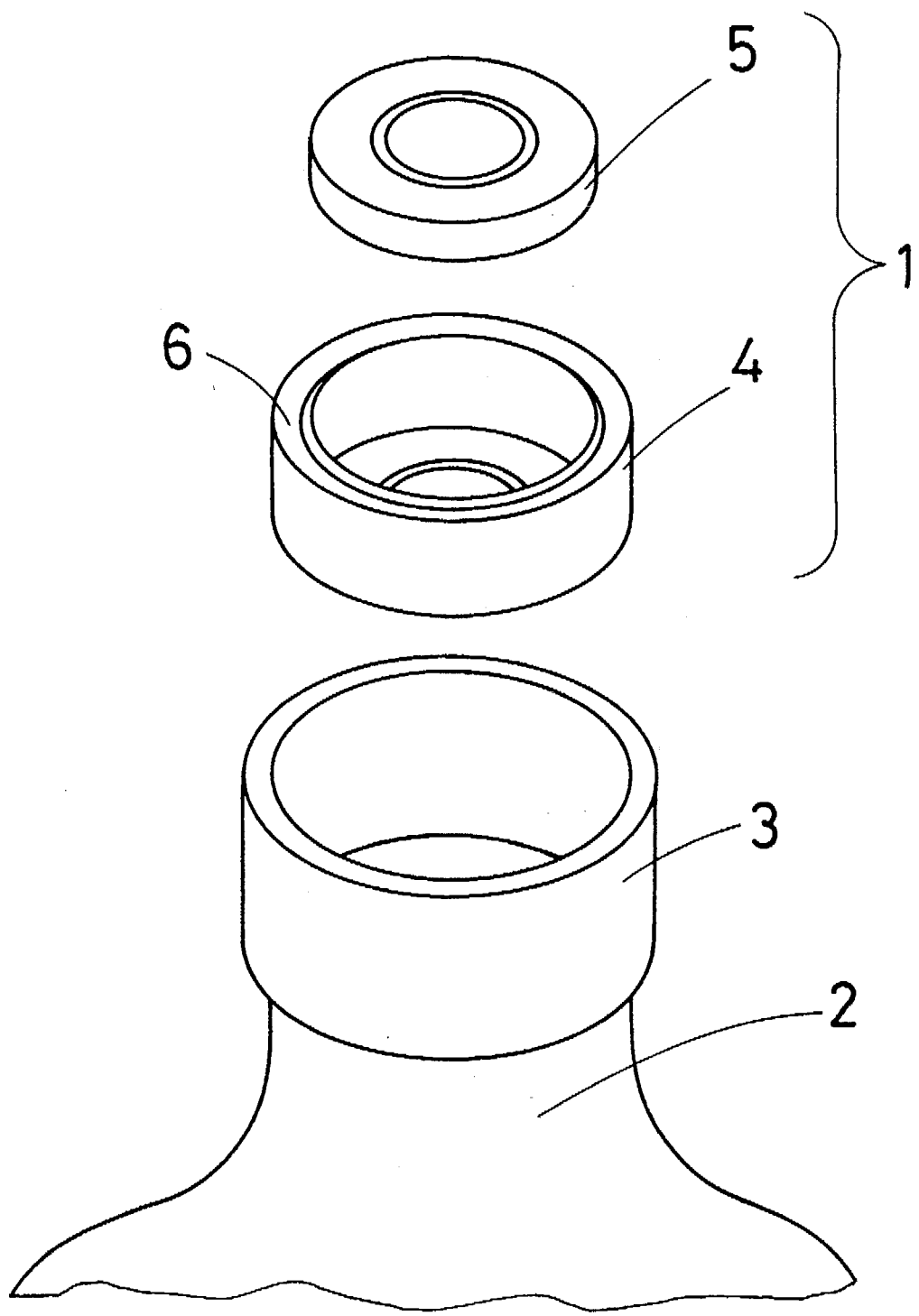
FIG. 1 is an exploded perspective view for illustrating a condition where a closure having a tight-sealing synthetic resin stopper and a leakage preventing rubber stopper is to be inserted in a mouthpiece of a synthetic resin container according to an example of the present invention.

Hereinafter, the present invention will be described by way of illustrating examples with reference to FIGS. 1 to 7.

A transfusion synthetic resin container 2 including a mouthpiece 3, sealed by a closure 1, is to be used for medical drip infusion or the like. The closure 1 has a tight-sealing synthetic resin stopper 4 and a leakage preventing rubber stopper 5. The leakage preventing rubber stopper 5 functions to prevent liquid leakage when the closure 1 is pierced by an instillation needle or the like.

Next, a method for sealing the mouthpiece 3 by the closure 1 having the synthetic resin stopper 4 and the rubber stopper 5 will be described.

Figure 2:
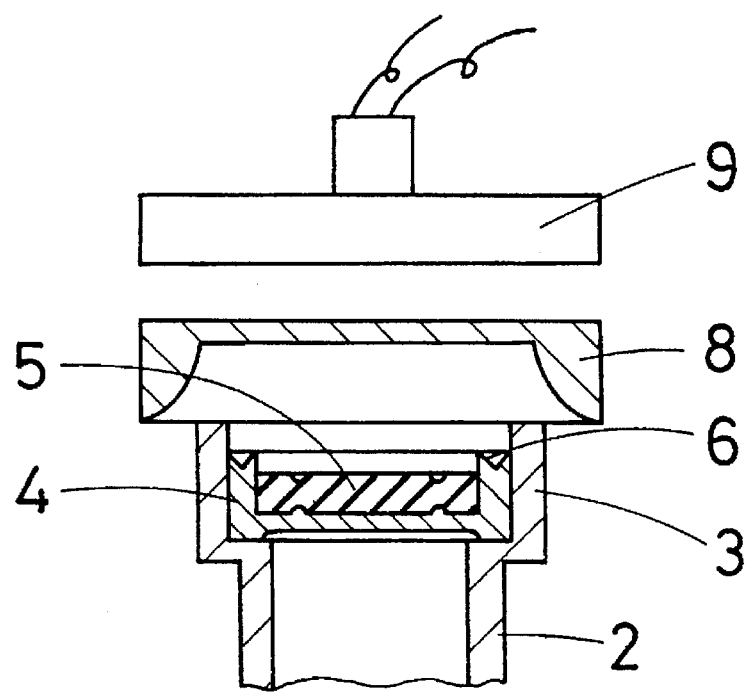
FIG. 2 is a partial cross-sectional view for illustrating a condition where the upper portions of the mouthpiece and the tight-sealing synthetic resin stopper are to be covered with a metallic mouthpiece forming cap and thermally welded using a welding heater according to the present invention.
Figure 3:
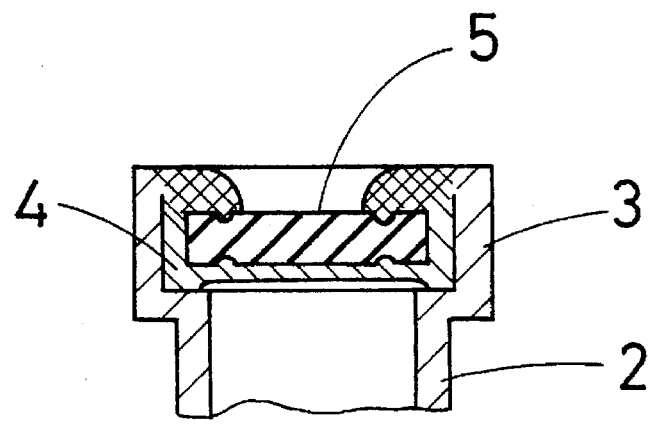
FIG. 3 is a partial cross-sectional view for illustrating a condition where the mouthpiece and the tight-sealing synthetic resin stopper are thermally welded so as to be integrated with each other and with the leakage preventing rubber stopper according to the present invention.

According to an example of the present invention, the upper portion of the synthetic resin stopper 4 is provided with a concave portion 6 having a wedge shaped cross-section as is shown in FIGS. 1 and 2. Thus, the upper portion of the synthetic resin stopper 4 is made hollow, in order to achieve excellent thermal conductivity.

Figure 4:
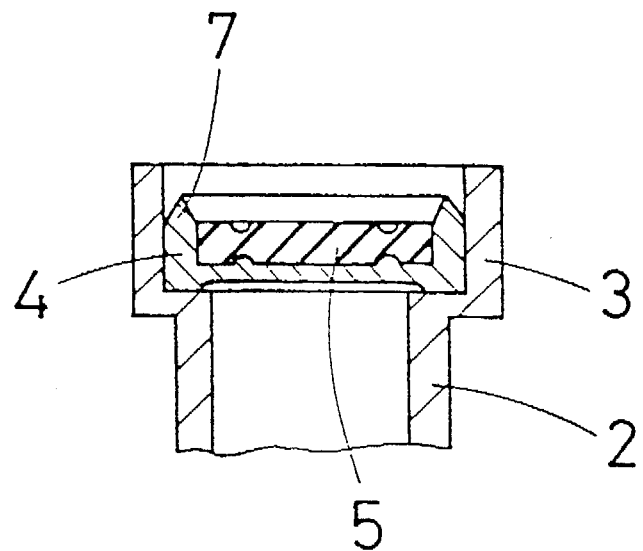
FIG. 4 is a partial cross-sectional view for illustrating another example of the present invention where the upper portion of the tight-sealing synthetic resin stopper is provided with a convex portion.

Alternatively, as is shown in FIG. 4, the upper portion of the synthetic resin stopper 4 may be provided with a convex portion 7 having a wedge-shaped cross-section, so that the thickness of the upper portion of the synthetic resin stopper 4 is made thinner, thereby achieving excellent thermal conductivity.

Herein, the cross-sections of the concave portion 6 and the convex portion 7 are both wedge-shaped. However, the shapes of the cross-sections of the concave portion 6 and the convex portion 7 are not limited to those shown in Figures, and various modifications are possible.

Figure 5:
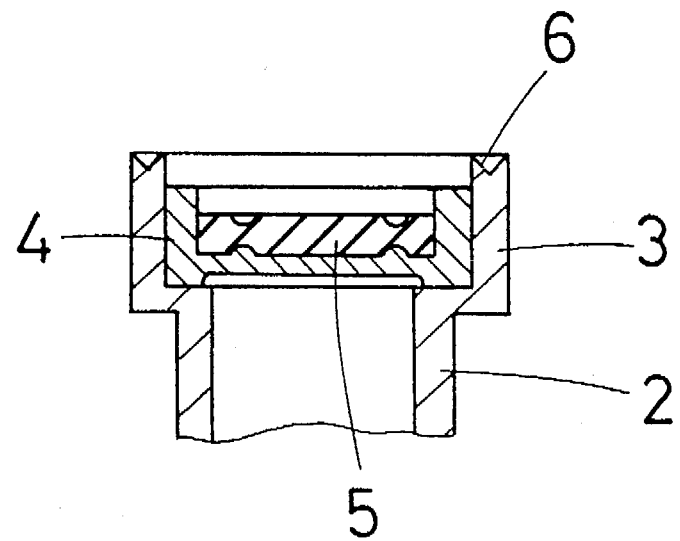
FIG. 5 is a partial cross-sectional view for illustrating still another example of the present invention where the upper portion of the mouthpiece is provided with a concave portion.
Figure 6:
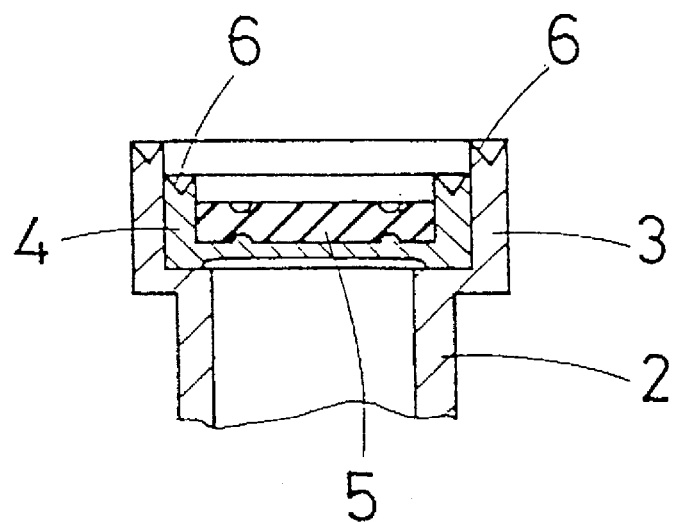
FIG. 6 is a partial cross-sectional view for illustrating still another example of the present invention where both of the upper portions of the tight-sealing synthetic resin stopper and the mouthpiece are provided with a concave portion.
Figure 7:
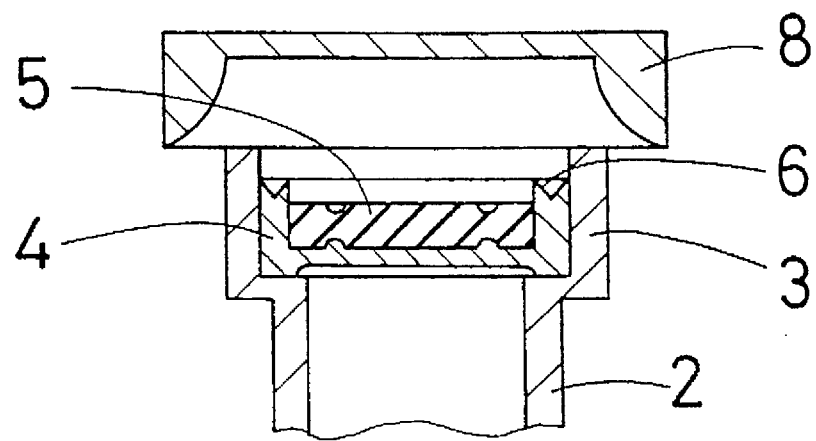
FIG. 7 is a partial cross-sectional view for illustrating a condition where the upper portions of the mouthpiece and the tight-sealing synthetic resin stopper are to be covered with a metallic mouthpiece forming cap and thermally welded only using heat generated at the mouthpiece according to the present invention.

In the illustrated example of the present invention, the concave portion 6 is provided only at the upper portion of the synthetic resin stopper 4 as shown in FIG. 2. In another example, the convex portion 7 is provided only at the upper portion of the synthetic resin stopper 4 as shown in FIG. 4. In still another example, the concave portion 6 is provided at only the upper portion of the mouthpiece 3 as shown in FIG. 5. In still another example, the concave portion 6 is provided in both of the upper portions of the mouthpiece 3 and the synthetic resin stopper 4 as shown in FIG. 6. However, the present invention is not limited to the above, and it is understood that the concave portion 6 and/or the convex portion 7 may arbitrarily be provided at one or both of the upper portions of the mouthpiece 3 and the synthetic resin stopper 4.

After the concave portion 6 and/or the convex portion 7 is provided at one or both of the upper portions of the mouthpiece 3 and the synthetic resin stopper 4 as is described above, the synthetic resin stopper 4 is inserted in the mouthpiece 3 and then the rubber stopper 5 is inserted in the synthetic resin stopper 4. Next, as is shown in FIG. 2, the upper portions of the mouthpiece 3 and the synthetic resin stopper 4 are covered with a metallic mouthpiece forming cap 8. Finally, the metallic mouthpiece forming cap 8 is pressed using a welding heater 9 so that the mouthpiece 3 and the synthetic resin stopper 4 are pressed inwardly and are thermally welded so as to be integrated with each other and with the rubber stopper 5. With the improved thermal conductivity provided by the concavities or convexities, the thermal welding process can be performed in a shorter time than in the prior art.

In addition, according to the present invention, it is also possible to perform the thermal welding process without using the welding heater. First, a concave portion and/or a convex portion is provided in the upper portion of the synthetic resin stopper 4, thereby imparting excellent thermal conductivity. In this case, a concave portion and/or a convex portion may also be provided in the upper portion of the mouthpiece. Next, the synthetic resin stopper 4 and the rubber stopper 5 are inserted in the mouthpiece. Thereafter, the upper portions of the synthetic resin stopper 5 and the mouthpiece 3 are covered with the metallic mouthpiece forming cap 8 as shown in FIG. 6. Then, the metallic mouthpiece forming cap 8 is pressed inwardly so that the upper portions of the synthetic resin stopper 4 and the mouthpiece 3 can be thermally welded only using heat generated at the mouthpiece 3. That is, the improved thermal conductivity of the synthetic resin stopper makes it possible to perform the thermal welding process by only utilizing heat generated at the mouthpiece while the mouthpiece is thermosoftened during a container molding process, thereby saving energy and simplifying the production process.

Various other modifications will be apparent to and can be readily made by those skilled in the art without departing from the scope and spirit of the present invention. The scope of the present invention is therefore to be limited only by the claims appended hereto.

What is claimed is:

1. A method of sealing a synthetic resin container, the method comprising:

forming a wedge-shaped concave or convex portion in the upper surface of at least one of a synthetic resin stopper and a mouthpiece of a container;

inserting the synthetic resin stopper into a mouthpiece of the container;

inserting a rubber stopper into the synthetic resin stopper;

covering the upper portions of the mouthpiece and the synthetic resin stopper with a metallic cap; and pressing the metallic cap so that the mouthpiece and the synthetic resin stopper are deformed inwardly and thermally welded utilizing only heat generated at the mouthpiece of the container during molding of the container, wherein the mouthpiece, the synthetic resin stopper, and the rubber stopper are integrated with each other.

2. The method as claimed in claim 1, wherein said forming operation further comprises forming a wedge-shaped concave or convex portion in both of the upper surfaces of the synthetic resin stopper and the container mouthpiece.

* * * * *

UNITED STATES PATENT AND TRADEMARK OFFICE
CERTIFICATE OF CORRECTION

PATENT NO. : 5,656,112
DATED : August 12, 1997
INVENTOR(S) : Nihee KURODA

It is certified that error appears in the above-indentified patent and that said Letters Patent is hereby corrected as shown below:

On the title page: Item [73] under Assignee, change "FUSO PHARMACEUTICAL INDUSTRIES, INC. to --FUSO PHARMACEUTICAL INDUSTRIES, LTD.--

Signed and Sealed this

Twenty-sixth Day of May, 1998

Attest:

BRUCE LEHMAN

Attesting Officer

Commissioner of Patents and Trademarks